US00PP30047P3

(12) United States Plant Patent
Biancheri

(10) Patent No.: US PP30,047 P3
(45) Date of Patent: Jan. 1, 2019

(54) ***RANUNCULUS* PLANT NAMED 'ABUMACATLO'**

(50) Latin Name: *Ranunculus asiaticus*
Varietal Denomination: ABUMACATLO

(71) Applicant: Alberto Biancheri, Camporosso Mare (IT)

(72) Inventor: Alberto Biancheri, Camporosso Mare (IT)

(73) Assignee: Impresa Individuale Biancheri, Alberto (IT)

( * ) Notice: Subject to any disclaimer, the term of this patent is extended or adjusted under 35 U.S.C. 154(b) by 0 days.

(21) Appl. No.: 15/731,510

(22) Filed: Jun. 20, 2017

(65) Prior Publication Data

US 2018/0042158 P1 Feb. 8, 2018

(30) Foreign Application Priority Data

Aug. 5, 2016 (QZ) ..... PBR 2016/1921

(51) Int. Cl.
*A01H 5/02* (2018.01)

(52) U.S. Cl.
USPC ..... Plt./263.1
CPC ..... *A01H 5/02* (2013.01)

(58) Field of Classification Search
USPC ..... Plt./263.1
CPC ..... A01H 5/02; A01H 5/00; A01H 6/72
See application file for complete search history.

(56) References Cited

PUBLICATIONS

Digital Flowers for Ranunculaceae, retrieved on May 10, 2018, retrieved from the Internet at http://www.life.illinois.edu/help/digitalflowers/Ranunculaceae/17.htm, one page. (Year: 2018).*
Hayden, Sepals and Petals and Stamens—Oh, My! or a brief discourse on putative homologies of perianth elements of Common Black Cohosh. Sempervirens Quarterly, Winter 2017, 8-9. (Year: 2017).*
Missouri Botanical Garden for *Ranunculus asiaticus*, retrieved on May 9, 2018, retrieved from the Internet at http://www.missouribotanicalgarden.org/PlantFinder/PlantFinderDetails.aspx?kempercode=a471, 2 pp. (Year: 2018).*

* cited by examiner

*Primary Examiner* — June Hwu
(74) *Attorney, Agent, or Firm* — Cassandra Bright

(57) ABSTRACT

A new and distinct *Ranunculus* cultivar named 'ABUMACATLO' is disclosed, characterized by vibrant yellow, extra double flowers. Plants produce an above average quantity of flowers of high quality throughout the flowering season. Flower size produced remains large throughout the flowering season. The new variety is a *Ranunculus*, normally produced as a cut flower and potentially useful as an ornamental plant.

2 Drawing Sheets

Figure 1:
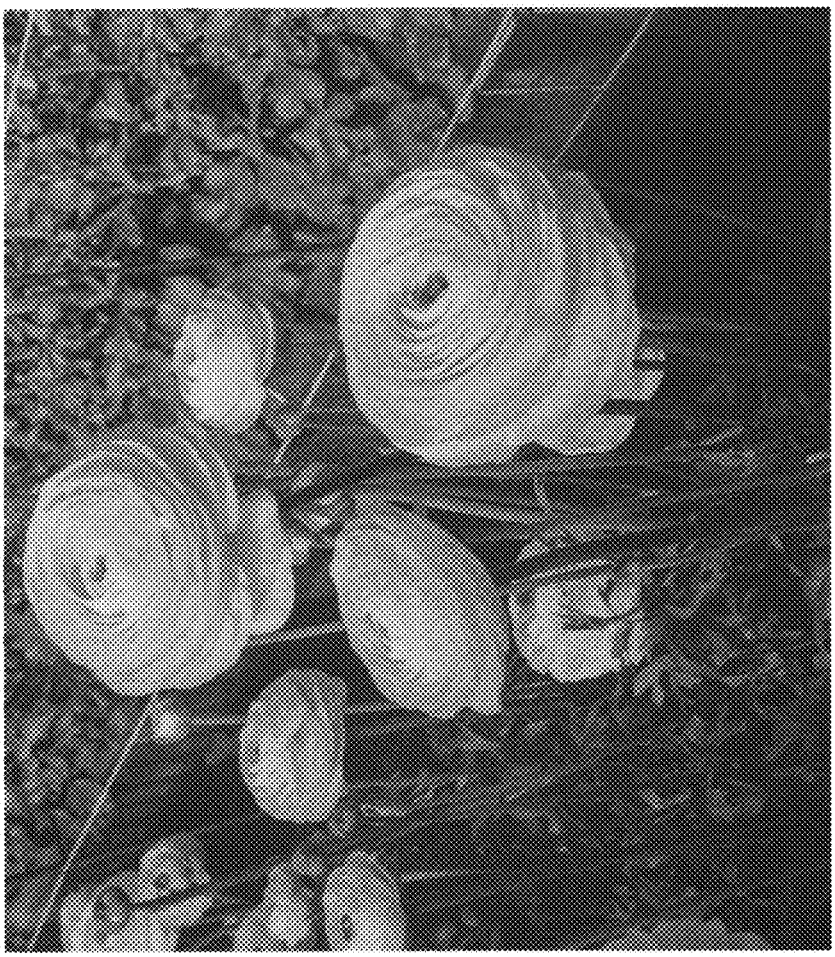

Latin name of the genus and species:
Ranunculus asiaticus.
Variety denomination: 'ABUMACATLO'.

BACKGROUND OF THE INVENTION

The new *Ranunculus* cultivar is a product of a planned breeding program conducted by the inventor, Alberto Biancheri in Camporosso Mare, Italy. The cross resulting in this new variety was made during 2008.

The seed parent is the, unpatented, proprietary variety referred to as *Ranunculus* 'G73-00/A'. The pollen parent is the unpatented, proprietary variety referred to as *Ranunculus* 'G141/1'. The new variety was discovered in 2012 by the inventor in a group of seedlings resulting from the 2008 crossing, in a research greenhouse in Camporosso Mare, Italy.

Asexual reproduction of the new cultivar was first performed by vegetative division of buds sprouting from the tuberous root of the selected plant. Subsequent propagation has been performed by tissue culture. First propagation took place at a research greenhouse in Camporosso Mare, Italy in 2012 and has shown that the unique features of this cultivar are stable and reproduced true to type in multiple successive generations.

SUMMARY OF THE INVENTION

The cultivar 'ABUMACATLO' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ABUMACATLO' These characteristics in combination distinguish 'ABUMACATLO' as a new and distinct *Ranunculus* cultivar:

1. Vibrant yellow flower color.
2. Large corolla produced throughout flowering season.
3. Extra double flower.
4. Above average quantity and quality of flower stems produced during the flowering season.

PARENT COMPARISON

Plants of the new cultivar 'ABUMACATLO' are similar to plants of the seed parent, in most horticultural characteristics, however, plants of the new cultivar 'ABUMACATLO' differ in the following;

1. Flower shape of the new variety is different. Gynoecium of the new variety is transformed to petals, forming a round structure in the center of flower, not seen in the seed parent.
2. Flower size of the new variety is larger. Flower size of the new variety is an average range of 8 to 10 cm, average flower size range of the seed parent is 6 to 8 cm.
3. Androecium of the new variety is transformed to petals, the seed parent has reduced stamens and good fertility.

Plants of the new cultivar 'ABUMACATLO' are similar to plants of the pollen parent, in most horticultural characteristics, however, plants of the new cultivar 'ABUMACATLO' differ in the following;

1. Flower shape of the new variety is different. Gynoecium of the new variety is transformed of petals, forming a round structure in the center of flower, not seen in the pollen parent.
2. Flower size of the new variety is smaller. Flower size of the new variety is an average range of 8 to 10 cm, average flower size range of the pollen parent is 6 to 8 cm.
3. Androecium of the new variety is transformed to petals, the pollen parent has reduced stamens and good fertility.

COMMERCIAL COMPARISON

Plants of the new cultivar 'ABUMACATLO' are comparable to the unpatented commercial variety *Ranunculus* 'ABCREAM'. The two *Ranunculus* varieties are similar in most horticultural characteristics; however, the new variety 'ABUMACATLO' differs in the following:

1. The corolla of the new variety has more petals.
2. Floral size of the new variety is smaller.
3. Floral color of the new variety is much deeper and brighter yellow.

BRIEF DESCRIPTION OF THE PHOTOGRAPHS

The accompanying photograph in FIG. 1 illustrates in full color flowering plants of the new variety at approximately five months old, grown in a greenhouse.

Figure 2:
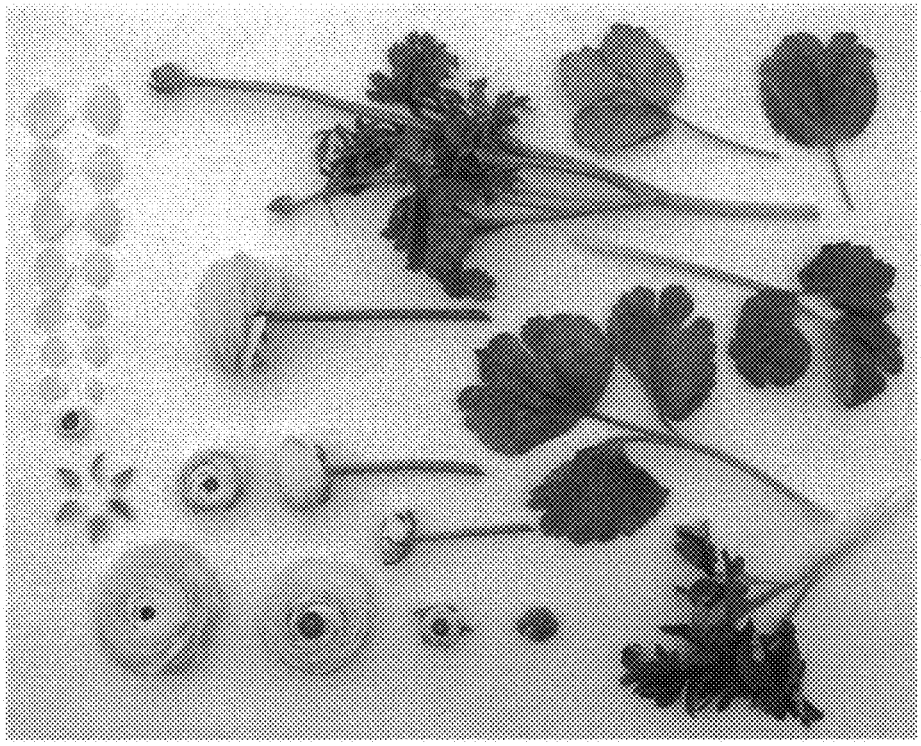

FIG. 2 illustrates a close up of plant parts.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 6$^{th}$ edition, except where general terms of ordinary dictionary significance are used. The following observations and measurements describe 'ABUMACATLO' plants grown in a greenhouse Camporosso Mare, Italy. The plant described has been cultivated under glass, planted in the months of September and described in the month of February. One must always refer to these conditions of season and culture, when considering the present description. By reason of different climate or culture conditions, differences may arise between certain characteristics of the plant and the corresponding characteristics of the description. It should be considered as normal and do not modify the essence of the present invention because it will possible to identify the plant by means of the totality of the characteristics given in the description. The tuberous root has been planted on raised benches in a peat and pumice substrate mixture. The growing temperature ranged from 12° C. to 25° C. during the day and from 2° C. to 8° C. during the night. General light conditions are bright, normal sunlight. Measurements and numerical values represent averages of typical plant types.

Botanical classification: *Ranunculus asiaticus* 'ABUMACATLO'.

PROPAGATION

Time to rooting: 15 days at approximately 10-12° C.

Time to produce a rooted plantlet: 20 days.

Root description: Tuberous roots. Quantity of tubers varies significantly with age and environmental factors. Colored tan and white, not accurately measured with an R.H.S. chart.

PLANT

Growth habit: Herbaceous perennial, robust plant, erect vegetation.

Height to top flower: 55 to 60 cm.

Plant spread: 30 to 40 cm.

Growth rate: Medium.

Branching characteristics: Main floral stems grow from a basal rosette with 1 or 2 lateral branches, each one of which has a flower.

Length of lateral branches: 50 to 55 cm.

Diameter of lateral branches: 0.6 to 0.8 cm.

Texture of lateral branches: Slightly tomentose.

Internode length: Internodes are extremely close together, forming a basal rosette.

Strength of lateral branches: Medium.

Color of lateral branches: Yellow Green (RHS 145A).

Angle of branches: 15° to 20°.

Number of leaves per lateral branch: Usually 2.

FOLIAGE

Leaf: The leaves, usually numerous, have a marked heterophyllia (significant variation in leaf shape, size and arrangement on a same plant). Simple, biternate and ternate leaves appear on the same plant, in relation to the degree of development (young leaf and mature leaf) and their position on the plant (basal leaf—leaf at the base of the plant—and cauline leaf—leaf inserted at the nodes of the floral stems).

Leaf at the base of the plant:

*Arrangement.*—Simple (young leaf, YL); Biternate (mature leaf, ML).

*Average length.*—22.0 to 32.0 cm.

*Average width.*—16.0 to 20.0 cm.

*Overall shape of blade.*—Obovate (young leaf); Palmatipartite (mature leaf).

*Dissected leaves, describe lobes, quantity of dissection.*—Young leaves are generally not lobed; mature leaves are generally divided in 3 parts, each one of which further divided in 3 or more lobes.

*Apex.*—Acute.

*Base.*—Rounded.

*Attachment.*—Base of the plant.

*Margin.*—Dentate (mature leaf).

*Texture of top surface.*—Slightly tomentose, verrucose.

*Texture of bottom surface.*—Slightly tomentose, verrucose.

*Appearance of top surface.*—Matte.

*Appearance bottom surface.*—Glossy.

*Leaf internode length*.—The internodes are extremely close together, forming a basal rosette.

*Color*.—Young foliage upper side: Green (RHS 138A). Young foliage under side: Yellow Green (RHS 148C). Mature foliage upper side: Green (RHS 138A). Mature foliage under side: Yellow Green (RHS 148C).

*Venation*.—Type: Dichotomous; plunging in to the limb at the upper surface; raised on the limb at the lower surface. Venation color upper side: Yellow Green (RHS 145A). Venation color under side: Yellow Green (RHS 145A).

*Petiole*.—Petiole: Long, tubular, rigid. Length: 13 to 22 cm. Diameter: 0.5 to 0.8 cm. Pubescence: Slightly tomentose.

*Color*.—Yellow Green (RHS 145A).

Leaf inserted at the nodes of the floral stems (sl):

*Arrangement*.—Biternate.

*Average length*.—16 to 22 cm.

*Average width*.—12 to 18 cm.

*Overall shape of blade*.—Palmatipartite.

*Dissected leaves, describe lobes, quantity of dissection*.—Generally divided in 3 parts, each one of which is further divided in many lobes.

*Apex*.—Acute.

*Base*.—Acute.

*Attachment*.—Floral stems.

*Margin*.—Dentate.

*Texture of top surface*.—Slightly tomentose.

*Texture of bottom surface*.—Slightly tomentose.

*Appearance of top surface*.—Matte.

*Appearance bottom surface*.—Glossy.

*Leaf internode length*.—7 to 14 cm.

*Color*.—Foliage upper side: Green (RHS 137B). Foliage under side: Green (RHS 138B).

*Venation*.—Type: Longitudinal, plunging in to the limb at the upper surface and raised on the limb at the lower surface. Venation color upper side: Yellow Green (RHS 145A). Venation color under side: Yellow Green (RHS 145A).

*Petiole*.—Petiole: Long, slightly flat, rigid. Length: 8 to 15 cm. Diameter: 0.4 to 0.6 cm. Pubescence: Slightly tomentose.

*Color*.—Yellow Green (RHS 145A).

FLOWER

Bloom period: Winter to Spring.

Vase life (cut flower): 10 to 15 days.

Persistent or self-cleaning: Self-Cleaning.

Number of flowers per plant: 6-8.

Bud:

*Closed bud* (*cb*).—Shape: Flattened globular, with a sharp point. Length: 1.2 to 2.3 cm. Diameter: 1 to 2 cm. Color: Yellow Green (RHS 144A).

*Slightly open bud* (*ob*).—Shape: Flattened globular. Length: 1.9 to 2.1 cm. Diameter: 2.0 to 2.3 cm. Color: Yellow Green (RHS N144B).

Flower size (of):

*Diameter*.—8 to 10 cm.

*Height*.—2.5 to 4.5 cm.

Corolla (of): Round, regular, in the form of a flat section.

Petals:

*Arrangement*.—Imbricated, disposed on the receptacle in very tight verticils. The size of the petals is quite variable, according to the position in the corolla, decreasing from the exterior toward the center. The average size of fully developed petal is as follows:

*Length*.—3.8 to 4.8 cm.

*Width*.—4.6 to 5.2 cm.

*Quantity*.—Double flower, petals are very numerous average range 120 to 160.

*Texture*.—Silky, thin, resistant.

*Apex*.—Rounded.

*Shape*.—Rounded deltoid to nearly orbicular.

*Margin*.—Entire or slightly Crenate.

*Aspect*.—Fan shape, concave, moderately reflexed when flower is fully opened.

Color when opening (cf):

*Upper surface*.—Yellow (RHS 12A).

*Lower surface*.—Yellow (RHS 12A).

Color fully opened (of):

*Upper surface* (*pu*).—Yellow (RHS 13A).

*Lower surface* (*pl*).—Yellow (RHS 13A).

Calyx to sepals (s):

*Quantity per flower*.—6 to 8.

*Shape*.—Concave, moderately incurved.

*Length*.—2.2 to 2.6 cm.

*Width*.—0.8 to 1.8 cm.

*Apex*.—Acute.

*Base*.—Flat to Slightly rounded.

*Margin*.—Entire.

*Texture*.—Lower surface is tomentose; Upper surface is glabrous.

*Color upper surface*.—Yellow Green (RHS 144A and N144A).

*Color lower surface*.—Yellow Green (RHS 144A).

Peduncle: None.

Pedicel:

*Length*.—50 to 55 cm.

*Diameter*.—1.0 to 1.2 cm.

*Color*.—Yellow Green (RHS 145A).

*Orientation*.—Upright, straight, rigid.

*Pubescence*.—Slightly tomentose.

Fragrance: None.

REPRODUCTIVE ORGANS

Androecium:

*Stamens*.—Almost absent.

*Quantity of andropetals*.—Andropetals indistinguishable from petals, quantity included with petals count.

*Nectar gland*.—Absent.

Gynoecium: The carpels are completely transformed in Strong Yellow Green (RHS 144B) leaves, which together form a nearly circular structure in the center of the corolla.

OTHER CHARACTERISTICS

Seeds and fruits: Seeds and fruit production not observed.

Disease and pest resistance: Neither resistance nor susceptibility to normal diseases and pests of *Ranunculus* has been observed.

Temperature tolerance: Upper and lower temperature tolerance not observed, plants have been grown in a climate controlled greenhouse. *Ranunculus asiaticus* typically tolerates temperatures within USDA Zones 7 to 11.

What is claimed is:

1. A new and distinct cultivar of *Ranunculus* plant named 'ABUMACATLO' as herein illustrated and described.

* * * * *